United States Patent [19]

Plaschy et al.

[11] Patent Number: 5,437,182
[45] Date of Patent: Aug. 1, 1995

[54] METHOD AND DEVICE FOR DETERMINING STRENGTH PROPERTIES OF THE WARP THREADS OF A WARP

[75] Inventors: Martin Plaschy, Hombrechtikon; Walter Krebs, Bad Ragaz, both of Switzerland

[73] Assignee: Zellweger Luwa AG, Uster, Switzerland

[21] Appl. No.: 122,522
[22] PCT Filed: Feb. 1, 1993
[86] PCT No.: PCT/CH93/00024
§ 371 Date: Sep. 28, 1993
§ 102(e) Date: Sep. 28, 1993
[87] PCT Pub. No.: WO93/06367
PCT Pub. Date: Aug. 19, 1993

[30] Foreign Application Priority Data
Feb. 7, 1992 [CH] Switzerland .............. 00363/92

[51] Int. Cl.⁶ .............................. G01N 3/08
[52] U.S. Cl. .............................. 73/160
[58] Field of Search ........... 73/160, 828, 830, 831, 73/833, 834

[56] References Cited

U.S. PATENT DOCUMENTS

| | | |
|---|---|---|
| 2,182,349 | 12/1939 | Pagnacco .............. 73/830 |
| 4,338,824 | 7/1982 | Brassel et al. . |
| 4,703,651 | 11/1987 | Mima .............. 73/160 |
| 4,805,276 | 2/1989 | Plaschy . |
| 4,825,702 | 5/1989 | Cizek .............. 73/828 |
| 5,050,437 | 9/1991 | Etter .............. 73/831 |

FOREIGN PATENT DOCUMENTS 0240074 10/1987 European Pat. Off. .
0403988 12/1990 European Pat. Off. .

*Primary Examiner*—Robert Raevis
*Attorney, Agent, or Firm*—Burns, Doane Swecker & Mathis

[57] ABSTRACT

The warp threads (Ka) are clamped as a thread layer, are divided off individually from this and are stretched with a simultaneous measurement of the tensile force and/or stretching. These operations take place before the weaving process in a step of the weaving preparation process in which the warp threads are in the form of a prepared warp-thread layer. The device contains means (1, 2) for clamping the warp-thread layer, means (4) for dividing off the warp threads and means (FP) for measuring the tensile force and/or stretching of the divided-off warp threads, the means (1, 2) for clamping the warp-thread layer forming an integral part of a warp preparation machine, preferably of a knotting unit or of a drawing-in unit.

21 Claims, 2 Drawing Sheets

METHOD AND DEVICE FOR DETERMINING STRENGTH PROPERTIES OF THE WARP THREADS OF A WARP

BACKGROUND OF THE INVENTION

FIELD OF THE INVENTION

The present invention relates to the determination of properties of threads and more particularly to the determination of strength properties of warp threads in a warp.

The tensile test of textile and industrial yarns has always been an important test in quality control, specifically as regards both staple yarns and filament yarns. This is because the results of the tensile test make it possible to draw conclusions as to the production and therefore reveal production deficiencies; tensile-force and stretch values give indications as to the suitability of the raw material used and allow prognoses for the further processing of the yarn and for the final product.

Tensile tests of this kind are nowadays carried out off-line in a textile laboratory by examining the various yarn batches by random sampling. A known appliance for the tensile testing of yarns and twines is the tensile-testing system USTER TENSORAPID (USTER—registered trademark of Zellweger Uster AG) described in U.S. Pat. No. 4,338,824, and another tensile-strength tester is known from EP-A-O,403,988.

Textile laboratories equipped with modern test appliances are to be found very frequently in spinning mills and somewhat rarely in weaving mills. The reason for their limited use in weaving mills is to be sought in that the known test appliances do not allow testing on warp beams, and in that the strength data of non-sized yarns do not give sufficient indications as to the running behaviour on a specific weaving machine with a specific article. However, the fact that strength data are of interest in weaving mills too is proved by EP-A-O,240,074 which relates to a device for determining the strength properties of weft yarn, by means of which, as a rule, an entire yarn bobbin is always tested and at the same time is also used up.

In contrast, no tensile-strength testers for warp threads which can be integrated into the fabric production process are known, although any warp-thread break leads to a machine stoppage, and therefore the quality control of warp yarns should be of vital interest to any weaving mill.

SUMMARY OF THE INVENTION

The present invention, which relates to a method and a device for determining strength properties of the warp threads of a warp, is to allow strength properties to be determined as efficiently as possible and in a manner integratable into the fabric production process. Here, "integratable into the fabric production process" means that the determination of the strength properties takes place not off-line in a textile laboratory, but on-line as near as possible to a machine of the fabric production process. That this strength test is also to involve a minimum of warp-thread material used up for it is self-evident.

The method according to the invention is characterised in that the warp threads are clamped as a thread layer, are divided off individually from the thread layer and are stretched, with a simultaneous measurement of the tensile force and/or stretching, and in that these operations take place before the weaving process in a step of the weaving preparation process in which the warp threads are in the form of a prepared warp-thread layer.

The device according to the invention for carrying out this method is characterised by means for clamping the warp-thread layer, means for dividing off the warp threads and means for measuring the tensile force and/or stretching of the divided-off warp threads, said means for clamping the warp-thread layer forming an integral part of a warp-preparation machine, preferably of a knotting unit or of a drawing-in unit.

The invention starts from the new finding that, for efficient strength testing, the warp threads must be prepared as a thread layer, from which they can be separated in a simple way and fed to the measuring device. To put this finding into practice, the invention makes use of the fact that such a prepared thread layer is present many times in the preparatory process of the weaving mill. Thus, for example, during knotting and during drawing in, where the warp threads are respectively clamped on a so-called knotting stand or on a drawing-in frame. Since a cutting off of the warp threads always takes place both during knotting and drawing in, these operations constitute an ideal interface for the strength test.

As is known, during knotting and during drawing in, the warp threads are worked off from the respective stand or frame and at the same time knotted or drawn in, thread residues no longer required for further processing remaining on one of the clamping elements of the clamping device. The strength test can then be carried out on these thread residues, with the result that the requirement of minimum material consumption is also satisfied in the best possible way.

The method according to the invention also affords, in addition to the quality control of warp yarns, the following possibilities: indirect quality control of the sizing process, comparison of the running-out warp and the new warp during the knotting process, determination of the relationship between the strength values and the number of warp-thread breaks, and an optimum setting of the weaving machine on the basis of the strength values determined. Because, according to experience, the strength values between sized and non-sized yarns differ sharply from one another, the use of the method according to the invention is also expedient when a strength test has been conducted on the non-sized yarn.

Practical experiences in the knotting process have shown that the warp threads are sometimes sized to a substantially greater extent in the middle of the warp than at the edge. This points to a faulty setting or to another defect of the sizing machine. Defects of this kind can be detected relatively early and objectively by using the method according to the invention.

Of course, as a rule, the strength values determined by means of the method according to the invention are not comparable to the standard values determined either with conventional tensile-strength testers or with the USTER TENSORAPID already mentioned. But this is unimportant in as much as these standard values are obtained on non-sized yarns and are therefore in any case of only limited evidential force for the manufacturer of sized yarns. It is essential that this manufacturer, that is to say the weaver, should acquire an aid which gives him strength values comparable with one another for his processing steps, that is to say for weaving preparation and for weaving.

BRIEF DESCRIPTION OF THE DRAWING FIGURES

The invention is explained in more detail below by means of exemplary embodiments and the drawings; in which:

FIG. 1 shows a diagrammatic top view of a knotting stand with two warps clamped on this and with a knotting machine equipped with a strength tester according to the invention, FIG. 2 shows a block diagram of the signal-evaluation circuit; and FIG. 3 shows a perspective representation of a cutout from an exemplary embodiment of a knotting machine equipped with a stretch tester.

DETAILED DESCRIPTION OF THE INVENTION

Figure 1:
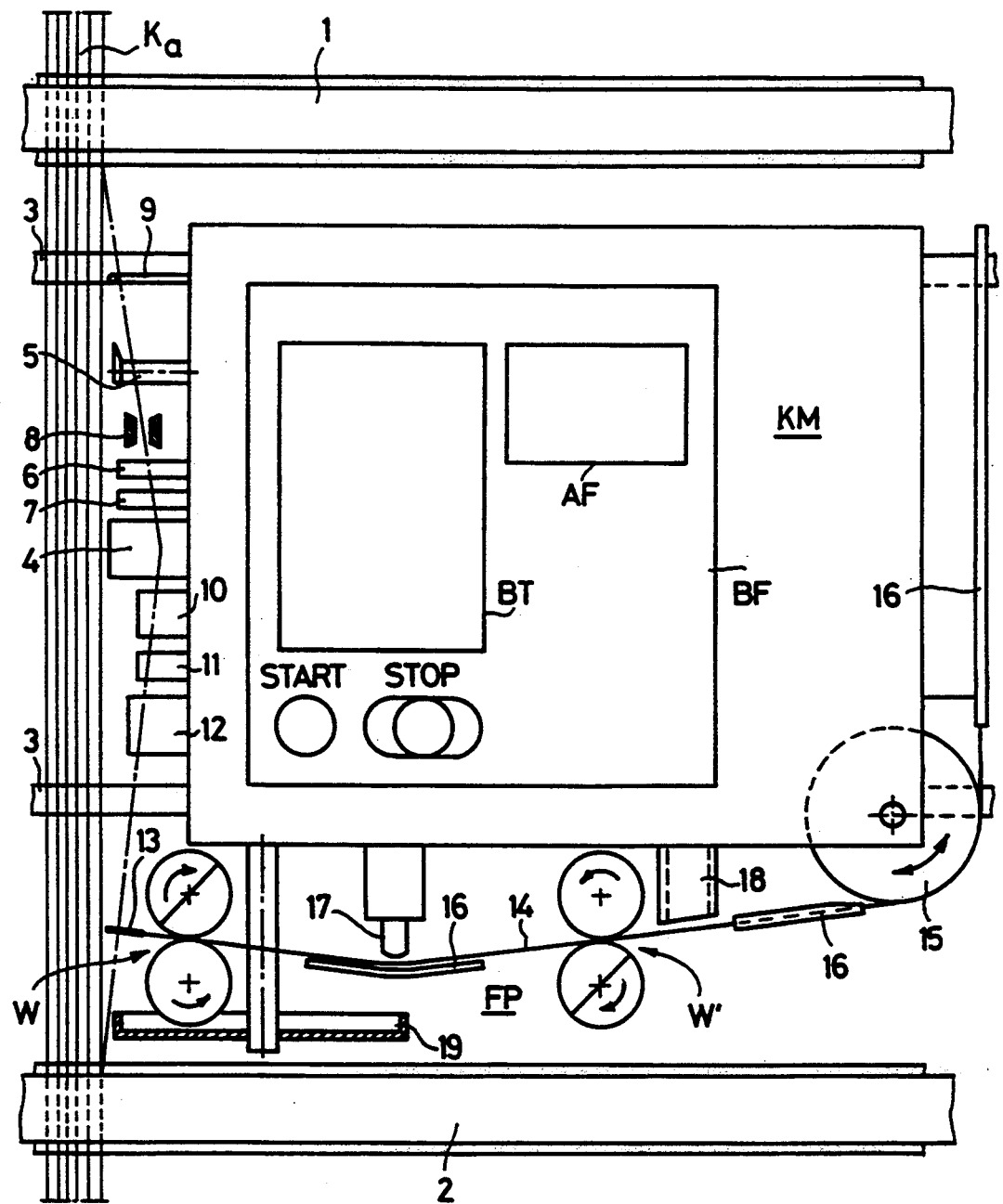

FIG. 1 shows a diagrammatic top view of a knotting stand, symbolised by two clamping rails 1 and 2, of the type used, for example, together with the warp-knotting machine USTER TOPMATIC. Clamped between the two clamping rails 1 and 2 are the warp threads Ka of a running-off warp beam, which are to be knotted, by means of a knotting machine KM moveable along the clamping rails, to the warp threads of a new warp beam. The latter are clamped between a second pair of clamping rails in a plane lying underneath the plane of the warp threads Ka, so that the warp threads Ka of the running-off warp beam, on the one hand, and the warp threads of the new warp beam, on the other hand, respectively form a sheet-like thread layer clamped in an ordered manner. This clamping is described, for example, in U.S. Pat. No. 4,805,276.

The individual clamping rails are mounted on suitable carrier arms (not shown) which are themselves connected to a movable basic stand via supporting columns, so that the knotting stand forms, in a known way, a movable frame having a trough-like top part. The latter contains, in addition to the clamping rails, two guide rails 3 with racks which are provided for the reception and forward movement of the knotting machine KM and for compensating movements of the lower thread layer. For the following description, the knotting machine USTER TOPMATIC is presumed to be known; attention is drawn in this respect to U.S. Pat. No. 4,805,276 already mentioned, in which essential parts of this knotting machine are described. In practical use, the knotting machine KM is placed onto the guide rails 3 at one of the two side edges of the two thread layers and is subsequently moved transversely relative to the thread layers, a thread Ka of the running-off warp always being knotted together with a thread of the new warp.

The knotting machine, on its upper covering surface confronting the attendant, has a control panel BF which contains, among other things, a control keyboard BT for entering various functions and calling up specific data, a start and stop button, indicator members for specific states and a display AF.

When a knotting machine is to be equipped with a strength tester, one of the most difficult problems to be solved is that of space, since the distance between the clamping rails 1 and 2 is predetermined by the conditions of space in the weaving shed and, in practice, cannot be increased.

In the exemplary embodiment illustrated in FIG. 1, the problem of space is solved by arranging the elements necessary for the knotting operation, in a way known in knotting machines, on the end face of the knotting machine KM confronting the thread layers, whereas the strength tester FP is mounted on one of the two longitudinal sides, specifically on that longitudinal side on which the thread residues remaining after the knotting operation are located. Another possibility for solving the problem of space would be to arrange the strength tester underneath the knotting elements, to be precise preferably in the vertical direction.

As mentioned in the introduction to the description, the means for clamping the warp-thread layer do not have to be formed by the knotting stand for a warp-knotting machine, but form an integral part or an accessory of a warp preparation machine, especially also of a drawing-in machine. Since drawing-in machines use, for clamping the warp-thread layer, drawing-in frames in which the distance between the clamping rails amounts to a multiple of the distance on a knotting stand, it is clear that the problems of space are less critical here. It will therefore be simple for the average person skilled in the art to arrange the strength tester, described below in connection with a knotting machine, on a drawing-in machine. This is true all the more because the mechanism used in knotting machines for dividing off the edge warp threads can also be used on drawing-in machines, as vouched for, for example, by WO-A-91/05099.

In FIG. 1, the following knotting elements known from the USTER TOPMATIC are shown diagrammatically, the individual elements being arranged, as a rule, in pairs, one for each thread layer: a thread-separating unit 4 which has essentially a dividing-off needle for each thread layer, a feeder for transporting the threads to the machine and, if appropriate, sensors for the detection of double threads (see U.S. Pat. No. 4,805,276); a common member 5 for both thread layers which has a drawing-in needle and a knotter mandrel; a pair of positively controlled thread clamps 6; two pairs of scissors 7; a so-called button twister 8; a knot extractor 9; a lease control 10 and an advance sensor 11, one for the upper and one for the lower thread layer.

The respective edge warp thread is divided off by the dividing-off needle of the thread-separating unit 4 and is brought by the feeder into the position represented by dot-and-dash lines in the Figure. The threads are then clamped by the thread clamps 6 and cut by the scissors 7. They are subsequently taken over by the button twister 8, the thread clamps 6 are released, and the threads are wound round the knotter mandrel and drawn by the drawing-in needle into the knotter mandrel. After the knot has been formed, the loose loop is tightened by the knot extractor 9 and the knotted threads are transported away.

The lease control 10 comes into operation in those instances in which a lease is required. Such a lease, as a rule a regular 1:1 lease, is necessary when the warp-thread density exceeds a particular limit or when particular special yarns, such as blaze or bouclé yarns, are being processed. In addition to 1:1 leases, however, irregular lease controls can also be worked off.

The advance sensor 11 is a mechanical sensor for the upper and the lower thread layer, which initiates the advance of the knotting machine KM or a movement of the lower thread layer towards the knotting machine. Shown on the side of the advance sensor 11 at the bottom in FIG. 1 is a member which is no longer necessary for the actual knotting operation, but which forms the interface with the strength tester. This member is a thread deflector 12 for each thread layer, which deflects the divided-off edge warp thread, clamped between the thread clamp 6 and the clamping rail 2, out of its thread layer in the vertical direction, specifically downwards out of the upper thread layer and upwards out of the lower thread layer, and which thereby reduces the distance between the edge warp threads. This deflection of the edge warp threads is carried out in order to feed them to a gripper needle 13 which is movable essentially transversely relative to the warp threads and which draws the warp threads into the strength tester FP after the termination of the knotting operation.

The gripper needle 13 is designed in the manner of a loop gripper known from weaving machines and has at its head end two hooks, of which one is intended for drawing in the upper edge warp thread and the other for drawing in the lower edge warp thread. The gripper needle 13 is carried by a flexible conveyor band 14 which is driven by a driving wheel 15 movable in oscillation. The driving wheel 15 is equipped on its circumference with stud-like projections which engage into corresponding recesses of the conveyor band 14. A driving mechanism of this type is known from gripper weaving machines and from WO-A-91/10003. The reference symbol 16 denotes a plurality of guide means for the conveyor band 14 which are arranged along the path of movement of the latter.

The strength tester FP is of the type described in EP-A-403,988 and contains two pairs of rollers W and W' which are at a distance from one another and which are intended for stretching the thread piece drawn in by the gripper needle 13, a force sensor 17 which is arranged between the pairs of rollers W and W' and which is preferably formed by a piezo electric sensor, and a suction nozzle 18 arranged after the rear pair of rollers W' in the drawing-in direction of the threads. This suction nozzle 18 serves, on the one hand, for taking over the thread from the gripper needle 13 and for tensioning it and, on the other hand, for sucking off the thread ends torn off during the strength test. All these parts of the strength tester FP are provided in pairs, specifically for the edge warp thread of the upper warp-thread layer and for the edge warp thread of the lower warp-thread layer. In the region of the front pair of rollers W, an extractor disc 19 common to the two parts of the strength tester FP is provided for the thread parts not torn off during the strength test.

Figure 2:
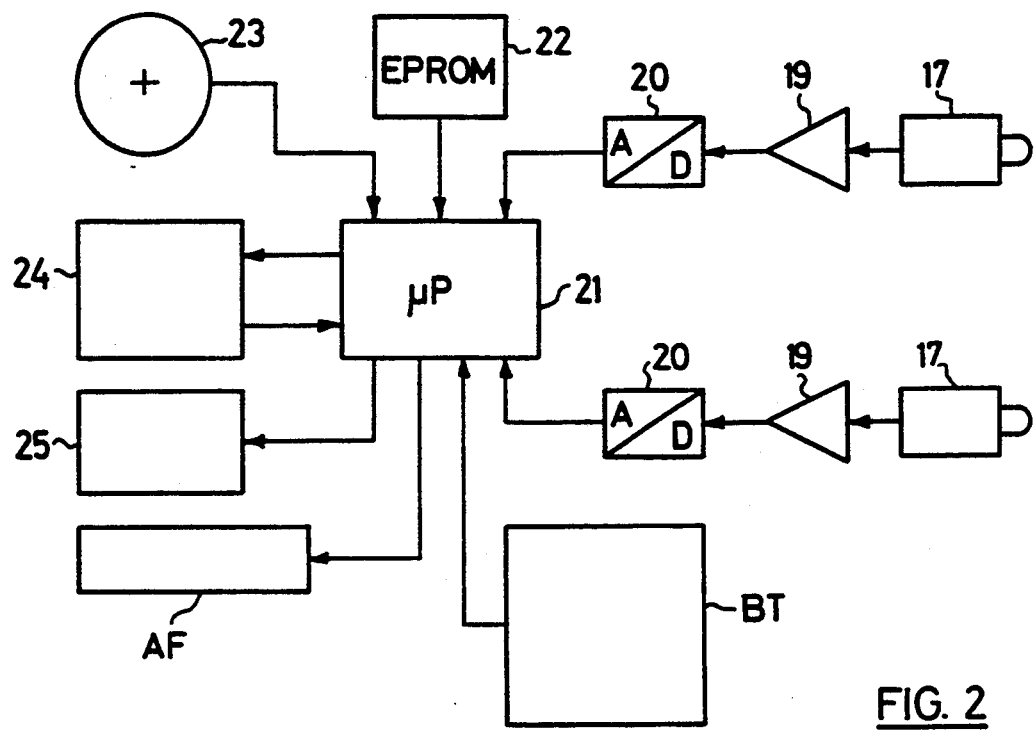

Each pair of rollers W, W' consists, in a known way, of a pressure roller and of a transport roller, of which the latter is formed in its region clamping the thread by a segment of a circle in the form of a semi-circle. There is, therefore, between the rollers of each pair of rollers a periodically opening and closing nip which, in the open state, allows the passage of the gripper needle 13 and conveyor band 14 and the drawing in of the thread and, in the closed state, clamps the thread. The drive of the pairs of rollers W, W' is synchronised with the drive of the driving wheel 15, on the one hand, and with the drive of the knotting machine KM, on the other hand. Since the drive of the knotting machine KM is variable, the rotational speed of the pairs of rollers W, W' as a rule is not constant, but is likewise variable. So that strength values measured at different rotational speeds of the pairs of rollers W, W' can be compared with one another, these are appropriately converted. This computing operation takes place in a microprocessor 21 (FIG. 2). One of the rollers of the front or of the rear pair of rollers W or W' or the driving wheel 15 is equipped with an incremental transmitter 23 (FIG. 2).

The combined knotting and strength-testing operation takes place essentially in the following five phases:

the first phase is a conventional knotting operation involving the steps of dividing off, transport of the divided-off threads to the knotting machine, clamping, cutting and knot formation. The thread ends knotted with one another are drawn away from the two thread layers by the knot extractor 9. With regard to FIG. 1, the knot is then located above the scissors 7, and underneath the latter relatively long thread ends extend as far as the clamping rail 2. The strength test commences at the same time and proceeds as follows:

the thread deflector 12 deflects the respective edge warp thread out of its thread plane and offers it to the gripper needle 13 which is moved by the conveyor band 14 forwards from its rear position in the region of the suction nozzle 18 towards the edge warp threads.

shortly after the cutting operation, the gripper needle 13 takes over the offered threads and draws them into the respective part of the strength tester FP, in this phase an open nip being formed between the rollers of the pairs of rollers W, W'. In the rear position of the gripper needle 13, the thread is fed to the suction nozzle 18 and is taken over by this and thereby tensioned.

immediately after this pre-tension has been applied, the thread is clamped between the rotating pairs of rollers W, W' and subsequently stretched to the tearing limit. The force occurring thereby is measured by the force sensor 17.

after the tearing of the thread, the torn-off thread residue is sucked off by the suction nozzle 18 and thus removed from the strength tester FP. The thread residue clamped by the front pair of rollers W is grasped by the rotating extractor disc 19 and drawn out of the pair of rollers. It then hangs down freely from the clamping rail 2, as is also the case in the currently used knotting machines without a strength tester. The strength tester FP is therefore ready for testing the strength of the next pair of threads which has been worked off in the meantime by the knotting machine. Instead of the extractor disc 19, a suction nozzle can also be provided for removing the thread residue remaining in the strength tester FP.

According to FIG. 2, the output signals from the two piezo electric sensors 17 are fed by way of an amplifier 19 and a A/D convertor 20 to two inputs of a microprocessor 21, the further inputs of which are connected to a program memory 22 formed, for example, by an EPROM, to the incremental transmitter 23 already mentioned, to a memory 24 and to the control keyboard BT, and the outputs of which are connected to said memory 24, to a data output 25 and to the display AF. Moreover, filters for filtering the signals from the piezo electric sensors 17 are provided.

The microprocessor 21 determines from the signals of the piezo electric sensors 17, for each thread, the tearing force, values for, for example, two points on the force/-stretch line, for the locating of which the incremental transmitter 23 is necessary, and derived quantities, such as, for example, the average tearing force or the fluctuations of the tearing force around an average value. All these values and quantities are filed in the memory 24 and can be extracted from this and displayed in any relationship. The latter is to be understood as meaning that strength values of a freely selectable number of warp threads can be displayed. Thus, for example, the total number of an assumed 5000 warp threads of a thread layer can be subdivided into groups, each of 500 threads, and the strength values mentioned displayed in groups.

Figure 3:
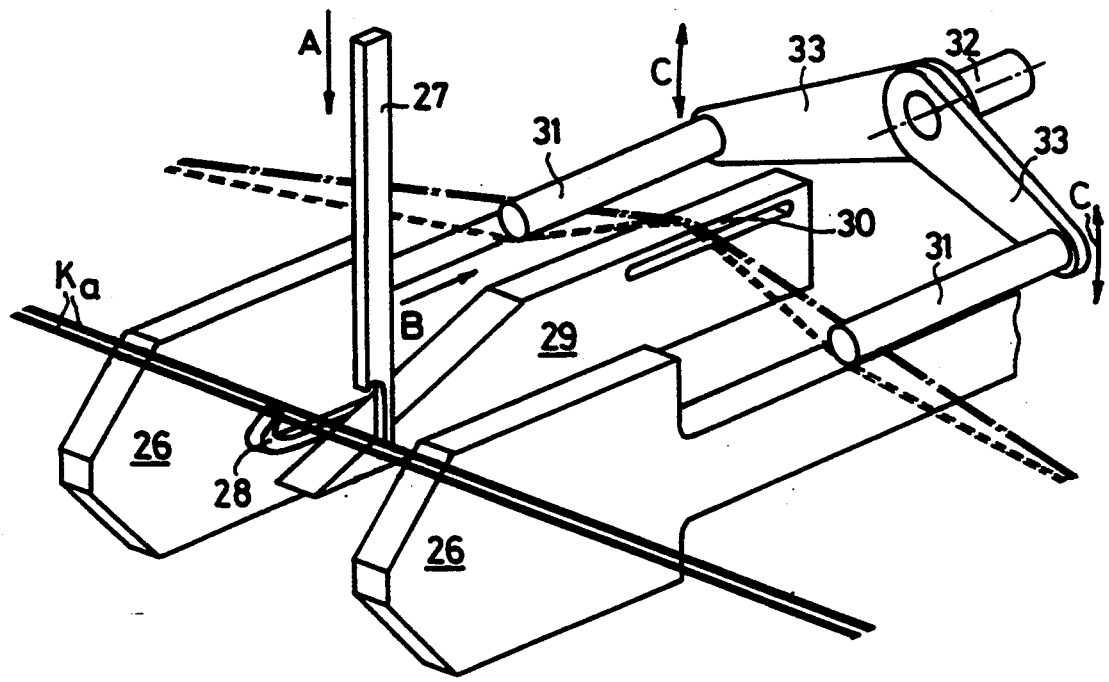

FIG. 3 shows a diagrammatic cutout from a warp-knotting machine equipped with a stretch tester, only the machine parts necessary for understanding the invention being represented. Here, therefore, there is no strength test, but a stretch test, this signifying a considerable simplification. The freely tensioned warp threads Ka are positioned just in front of two plate-like or rail-like guides 26 located at a distance from one another and, in order to be divided off from their thread layer by a dividing-off needle 27, are deflected so far out of the plane of the thread layer in the direction of the arrow A that they come level with the jaw of a thread feeder 28 equipped with a hook.

The thread feeder 28 is then moved away from the edge of the thread layer in the direction of the arrow B, at the same time grasps the divided-off thread Ka with its hook and draws it away from the thread layer into the position represented by dot-and-dashed lines. During this displacement, the thread passes over the guides 26 onto a force-measuring part 29 which is arranged between the guides and which is equipped with a pressure-sensitive member 30 in the region of its upper edge guiding the thread. This member 30 can be formed, for example, by a leaf spring or by a rigid pressure pick-up mounted resiliently on the force-measuring part 29.

Attention is drawn in this respect to U.S. Pat. No. 4,805,276 already mentioned, in which it is disclosed that the leaf spring forming the member 30 or, if the member 30 is made rigid, the spring carrying it is equipped with strain gauges or with piezo electric sensors sensitive to bending.

As soon as the thread slides along the part 30, it is pushed under two finger-like thread tensioners 31 which are arranged on both sides of the part 30 and parallel to this and which, in their position of rest, are located above the thread. When the thread has reached its end position on the part 30, it is released by the thread feeder 28 which is subsequently moved again into its initial position shown in the Figure.

Immediately after the release of the thread, the thread tensioners 31, which are fastened on arms 33 pivotable about a common shaft 32 in the direction of the arrows C, are pivoted downwards and press the thread downwards into the position represented by dashes. As a result of the tensioning of the thread, a force is exerted on the part 30 and generates a corresponding signal from said sensors which is a measure of the stretching of the thread. The signals from the sensors are processed according to the signal evaluation described with reference to FIG. 2, but the incremental transmitter 23 is no longer absolutely necessary.

What is claimed is:

1. Method for determining strength properties of warp threads of a warp, comprising clamping a plurality of warp threads to form a warp thread layer, individually dividing off warp threads from the warp thread layer, stretching the divided off warp thread and simultaneously measuring at least one of the tensile force and the stretching of the divided off warp thread, said steps of clamping, dividing off, stretching and measuring taking place before a weaving process and in a step of a weaving preparation process in which the warp threads are in the form of a prepared warp-thread layer.

2. Method according to claim 1, wherein the determination of the strength properties takes place during knotting of the warp threads to warp threads of a running-off warp and is carried out on a cut-off thread residue of each warp thread which remains after the knotting.

3. Method according to claim 2, wherein for each warp thread, the tensile force and the stretching are determined at different points.

4. Method according to claim 3, wherein said measuring step involves measuring the stretching of the warp threads, and including deriving further quanities from the measured stretching and outputting said further quanities, said further quanities including at least one of an average stretching of the warp threads and fluctuations in the stretching of the warp threads with respect to an average value.

5. Method according to claim 3, wherein said measuring step involves measuring the tensile force of the warp threads, and including deriving further quantities from the measured tensile force and outputting said further quantities, said further quantities including an average tensile force and fluctuations of the tensile force with respect to an average value.

6. Method according to claim 3, wherein values of the measured stretching and the measured tensile force are outputted either individually or for selectable groups of warp threads.

7. Method according to claim 1, wherein the determination of the strength properties takes place during drawing in of the warp threads and is carried out on a cutoff thread residue of each warp thread which remains after drawing in.

8. Device for determining strength properties of warp threads of a warp comprising clamping means for clamping warp threads to form a warp-thread layer, dividing off means for dividing off warp threads from the warp thread layer, measuring means for measuring at least one of the tensile force and the stretching of the divided-off warp threads, said clamping means forming an integral part of a warp preparation machine.

9. Device according to claim 8, wherein said warp preparation machine is a knotting unit that includes a knotting stand, the clamping means for clamping the warp-thread layer being formed by the knotting stand of the knotting unit.

10. Device according to claim 9, including a force measuring part, guides spaced apart from one another along which the divided-off threads are guided, thread feeders for transporting the divided off threads along the guides to the force-measuring part, and adjustable thread tensioners for stretching the divided off threads.

11. Device according to claim 10, wherein the force-measuring part has a guide edge for guiding the divided off threads, said guide edge being provided with a pressure-sensitive member, and including thread tensioners arranged on both sides of the force-measuring part and pivotable against the guide edge.

12. Device according to claim 9, wherein said measuring means is a strength tester for determining a tearing strength of the divided off threads, and including means for transferring the divided off threads to the strength tester.

13. Device according to claim 12, wherein said clamping means includes two clamping rails, one of said clamping rails being located at a greater distance from a knot former on the knotting machine which forms knots, the strength tester being arranged along one side face of the knotting machine which is adjacent to said one clamping rail.

14. Device according to claim 13, wherein the strength tester includes two pairs of rollers which are spaced apart from one another and rotatable in opposite directions and a force sensor disposed between the two pairs of rollers, the divided off thread being drawn between and clamped between the pairs of rollers and extending past the force sensor, each pair of rollers being adapted to alternately form an open nip between the roller of the pair for passage of the divided off warp thread and a closed nip between the rollers of the pair for clamping the divided off warp thread.

15. Device according to claim 14, wherein the means for transferring the threads to the strength tester includes a gripper needle.

16. Device according to claim 15, wherein the gripper needle is carded by a flexible driving band, said gripper needle having a hook for taking up the divided off thread.

17. Device according to claim 16, including a thread deflector for deflecting the divided-off thread out of the plane of the warp-thread layer to a level at which is located the hook of the gripper-needle.

18. Device according to one of claim 15, including grasping means for grasping the thread which is drawn into the strength tester by the gripper needle.

19. Device according to claim 18 wherein said two pairs of rollers include a front pair of rollers and a rear pair of rollers, said grasping means being a suction nozzle arranged after the rear pair of rollers with respect to the direction in which the thread is drawn between the two pairs of rollers.

20. Device according to one of claim 15, wherein said two pairs of rollers includes a front pair of rollers and a rear pair of rollers, and including thread residue removing means arranged adjacent the front pair of rollers for removing thread residue remaining in the strength tester after the strength of the warp thread has been tested by the strength tester.

21. Device according to claim 20, wherein said thread residue removing means is at least one of a rotatable extractor disc and a suction nozzle.

* * * * *